United States Patent [19]

Palsulich

[11] Patent Number: 4,676,467
[45] Date of Patent: Jun. 30, 1987

[54] APPARATUS FOR SUPPORTING A FLUID FLOW CASSETTE

[75] Inventor: William G. Palsulich, Boulder, Colo.

[73] Assignee: Cobe Laboratories, Inc., Lakewood, Colo.

[21] Appl. No.: 793,564

[22] Filed: Oct. 31, 1985

[51] Int. Cl.$^4$ .............................................. B01D 35/00
[52] U.S. Cl. .............................. 248/221.3; 248/311.2
[58] Field of Search ............... 248/221.3, 220.2, 311.2, 248/316.1, DIG. 1, 542; 210/321.3; 422/44, 46, 48

[56] References Cited

U.S. PATENT DOCUMENTS

| | | | |
|---|---|---|---|
| 4,191,351 | 3/1980 | Goyne | 248/311.2 |
| 4,225,438 | 9/1980 | Miller et al. | 210/321.3 |
| 4,412,916 | 11/1983 | Kell | 210/321.3 X |
| 4,436,620 | 3/1984 | Bellotti et al. | 210/321.3 X |
| 4,556,489 | 12/1985 | Diettrich, Jr. et al. | 210/321.3 |

Primary Examiner—Ramon S. Britts
Assistant Examiner—Karen J. Chotkowski

[57] ABSTRACT

Apparatus for supporting a fluid flow cassette having an opening for receiving a sensor, the apparatus including a sensor mounted on a support, means to lock the cassette into an insertion position with its opening aligned with but spaced from the sensor along an insertion axis, means to move the sensor relative to the opening to cause the sensor and opening to be brought together, and means to prevent the sensor and opening from coming close enough for the sensor to sealably engage the opening until after the cassette has been locked into the insertion position.

14 Claims, 8 Drawing Figures

APPARATUS FOR SUPPORTING A FLUID FLOW CASSETTE

FIELD OF THE INVENTION

The invention relates to apparatus for supporting a fluid flow cassette having an opening for receiving a sensor.

BACKGROUND OF THE INVENTION

Disposable or reusable fluid flow devices, such as cassettes that receive a patient's blood, can be mounted into position on medical machines for interaction with pumps, valves, and pressure and other sensors.

SUMMARY OF THE INVENTION

I have discovered that a sensor mounted on a machine can be accurately mated with an opening of a fluid flow cassette without danger of damage to the sensor or to the cassette during loading by an operator by providing a mechanism to lock the cassette into a insertion position with its opening aligned with but spaced from the sensor along an insertion axis and a mechanism to move the sensor toward the opening to sealably engage the opening only after the cassette has been locked into the insertion position.

In preferred embodiments, the sensor is mounted on a movable support plate that is slidably mounted relative to the locking mechanism; the locking mechanism includes jaws that extend from the front of and are pivotally mounted on a faceplate, and are adapted to engage a portion of the cassette; the jaws can only be opened if the movable support plate is spaced from the faceplate; the jaws have rear extensions with cam surfaces causing the extensions to be separated from each other and the jaws to be closed as a pin on the support plate carrying the sensor acts on them; and the jaws have guidance surfaces at the front to guide a portion of the cassette into a cavity between them.

Other advantages and features of the invention will be apparent from the following description of a preferred embodiment and from the claims.

DESCRIPTION OF THE PREFERRED EMBODIMENT

The drawings will be briefly described first.

Drawings

STRUCTURE

Figure 1:
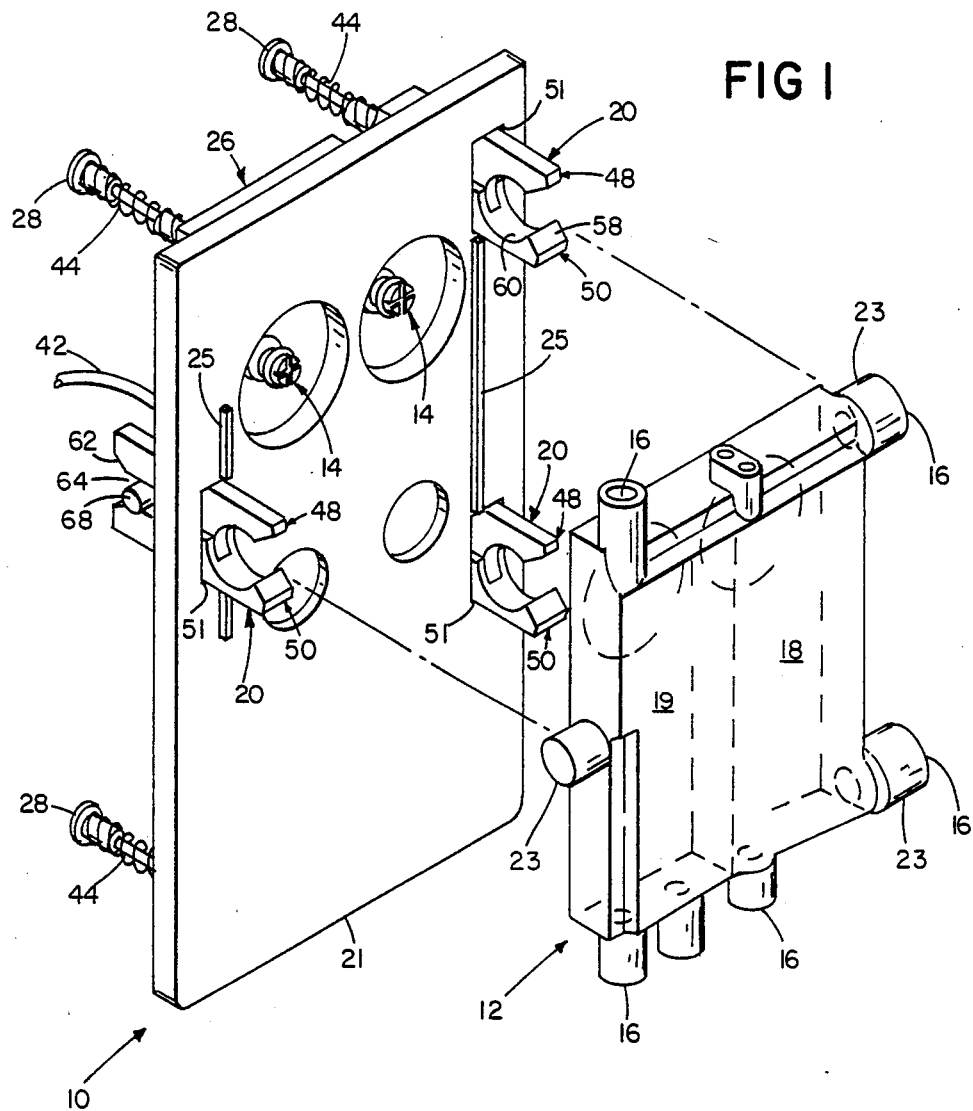
FIG. 1 is a diagrammatic perspective view showing apparatus for supporting a fluid flow cassette according to the invention.
Figure 8:
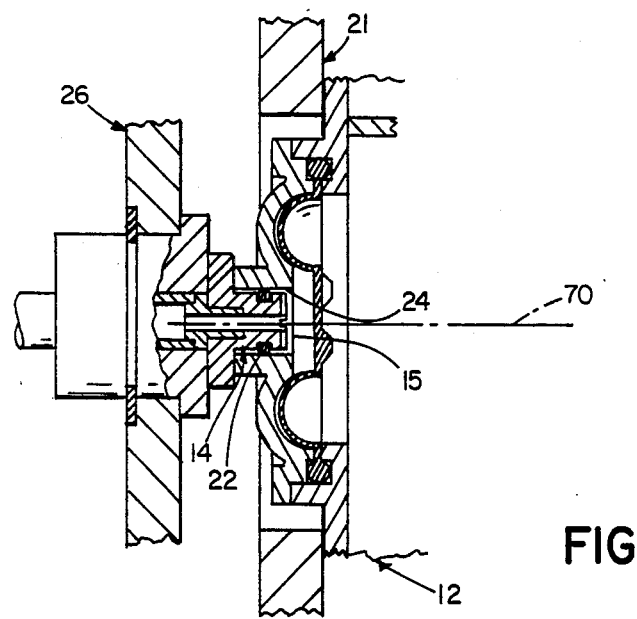
FIG. 8 is a partial sectional view showing a sensor of the FIG. 1 apparatus sealably engaging a wall defining an opening of the cassette.
Figure 2:
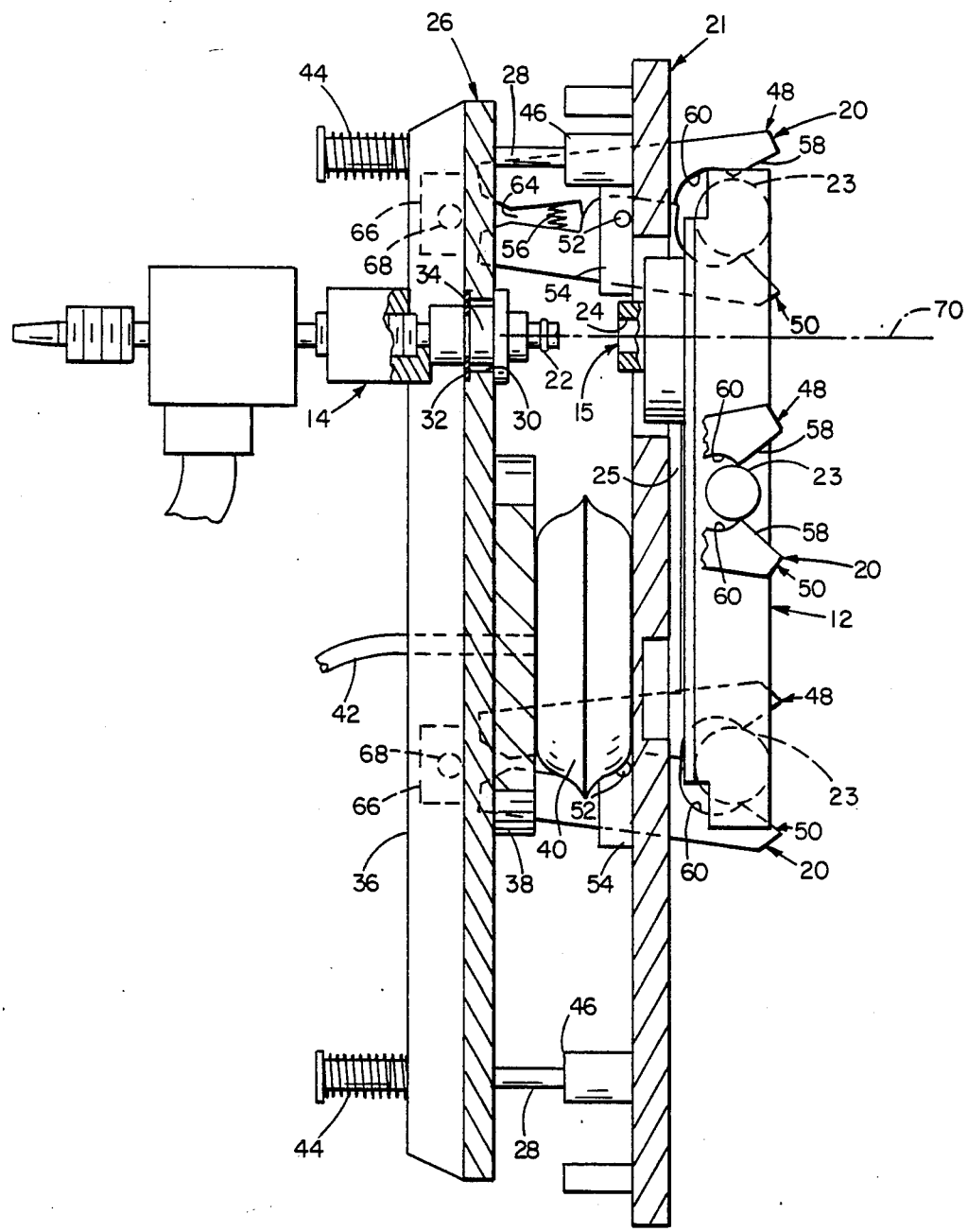
FIG. 2 is a vertical sectional view, taken at 2—2 of FIG. 4, of the FIG. 1 apparatus and cassette in an initial mounting position.

Referring to FIGS. 1 and 2, there is shown apparatus 10 for supporting plastic fluid flow cassette 12 having openings 15 on the rear surface for receiving sensors 14 of apparatus 10. Apparatus 10 is mounted on a dialysis machine (not shown). Cassette 12 includes inlet and outlet ports 16 for connection to inlet and outlet tubing carrying blood to and from chambers 18, 19. Apparatus 10 has three plastic jaws 20 that extend from plastic faceplate 21 and engage the two circular extensions 23 providing ports 16 on the right side of cassette 12 and a third circular extension 23 on the left side. Extending from the front of support plate 21 are parallel guidance ribs 25 adapted to engage the sides of cassette 12. As is seen in FIG. 8, sensors 14 have O-rings 22 for sealably engaging the inner mating cylindrical surfaces 24 of openings 15.

Figure 3:
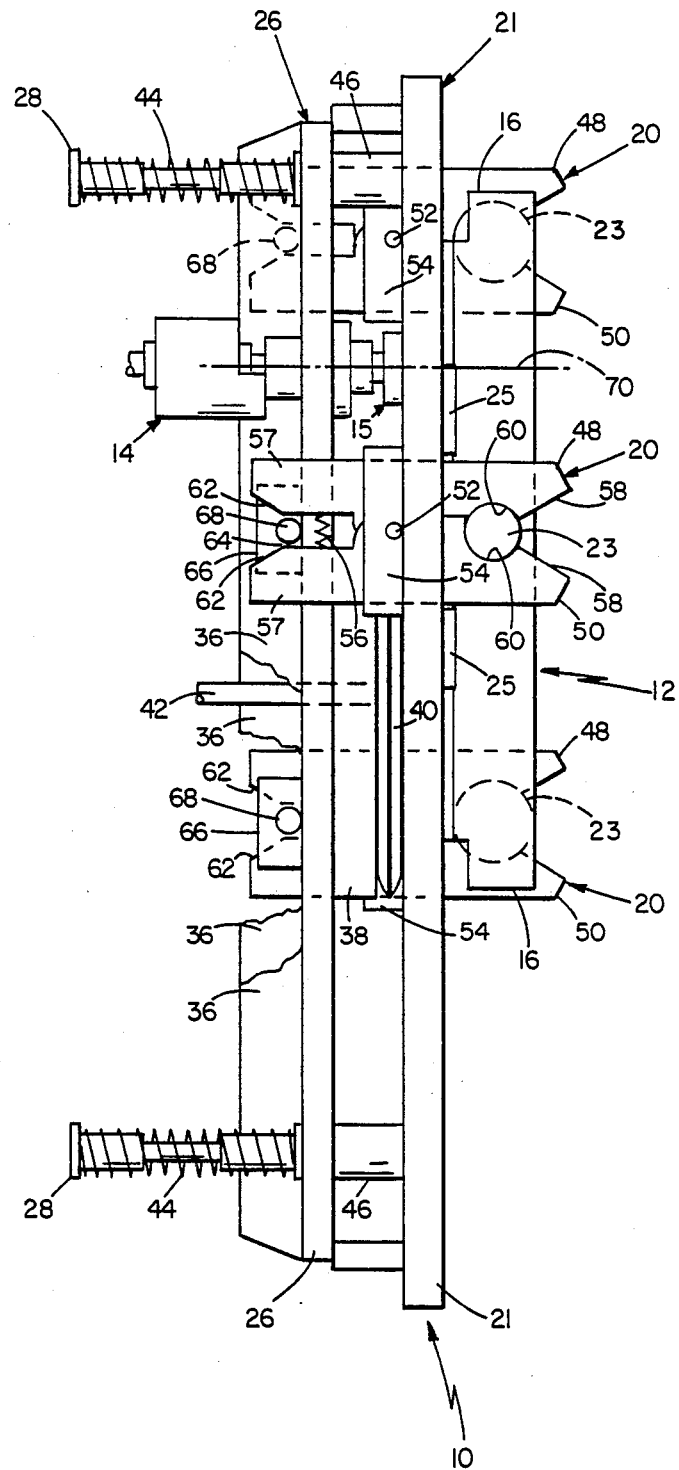
FIG. 3 is a side elevation of the FIG. 1 apparatus and cassette in a loaded position.
Figure 4:
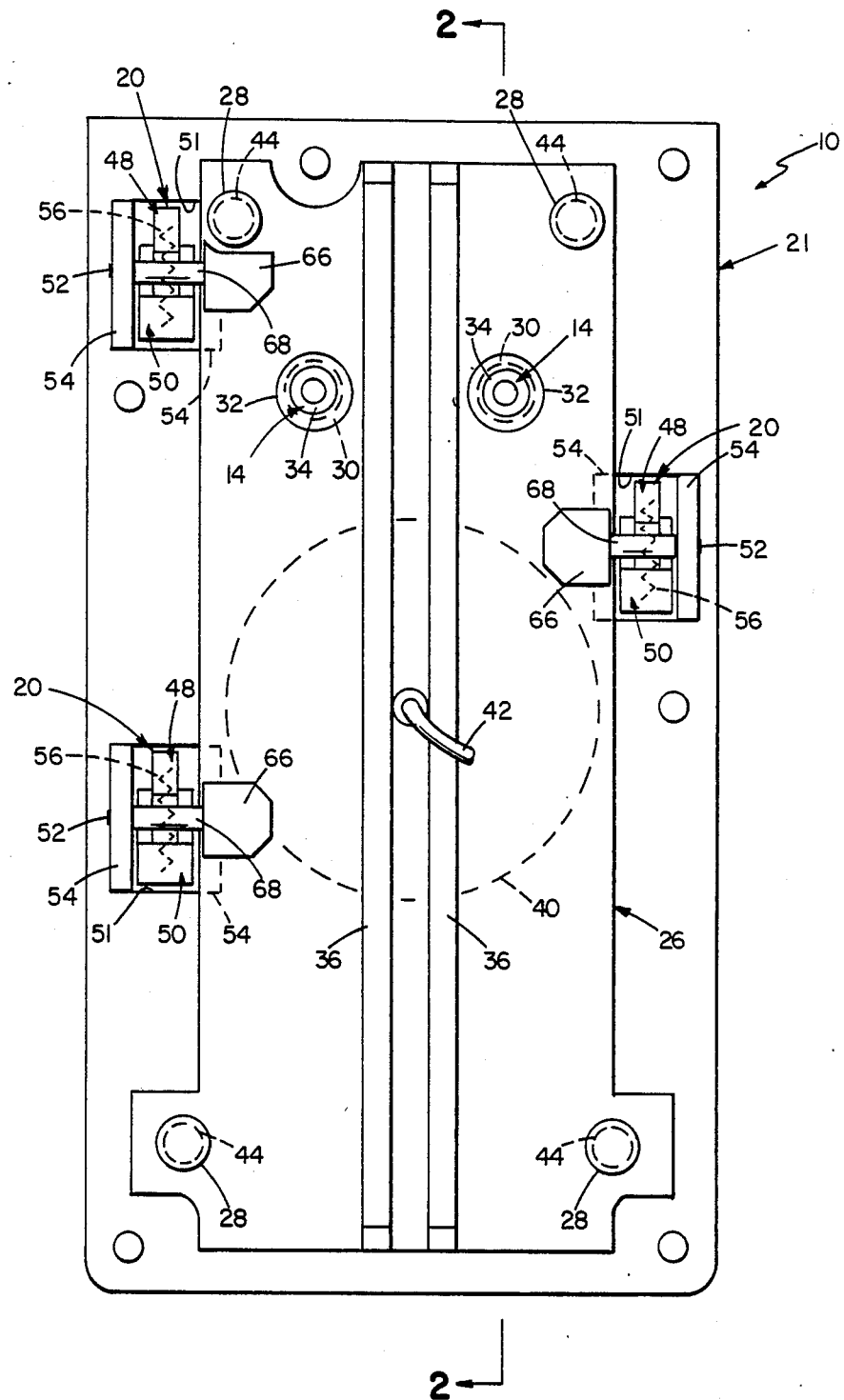
FIG. 4 is a rear elevation of the FIG. 1 apparatus.

Referring to FIGS. 2-4, it is seen that sensor 14 is supported by movable plastic support plate 26, which is slidably mounted on metal rods 28 secured to faceplate 21. Sensor 14 passes through hole 30 of support plate 26 and is held in position by clip 32. There is a slight clearance between hole 30 and the portion of sensor 14 passing through it, and this permits slight lateral movement of sensor 14. Plastic ribs 36 are provided on the back of support plate 26 for strength. Mounted on the front of support plate 26 on block 38 is expandable bladder 40, which is connected to air tube 42 and is used to separate support plate 26 from faceplate 21. Compression springs 44 are mounted on rods 28 and act to bias support plate 26 toward faceplate 21. Stops 46 limit the forward movement of support plate 26 toward faceplate 21, as is shown in FIG. 3.

Figure 5:
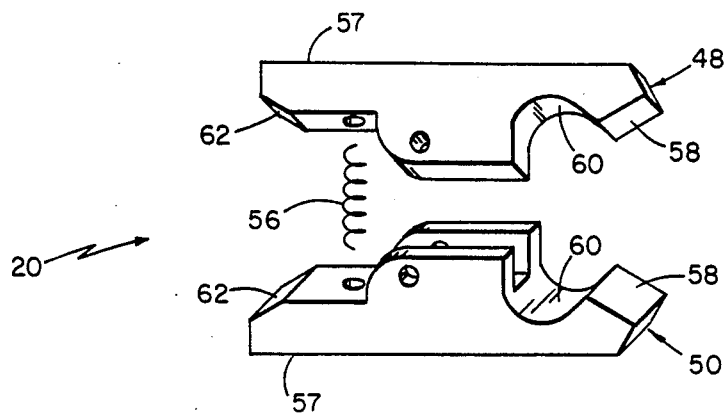
FIG. 5 is an exploded diagrammatic perspective view of jaws of the FIG. 1 apparatus.
Figure 6:
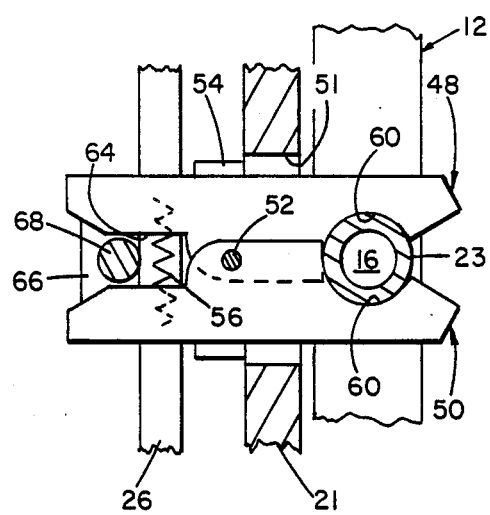
FIG. 6 is a diagrammatic view of the FIG. 5 jaws in a closed position.
Figure 7:
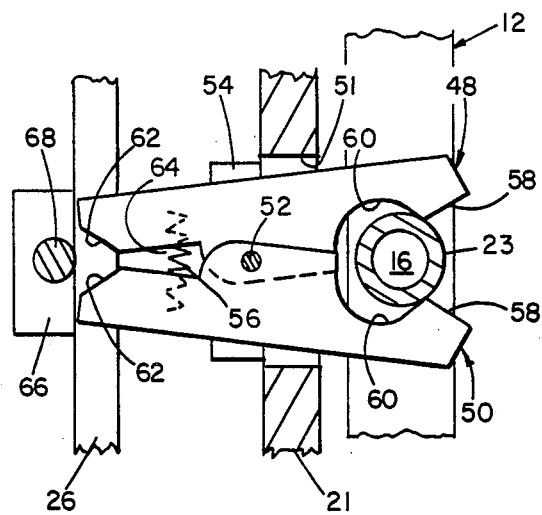
FIG. 7 is a diagrammatic view of the FIG. 5 jaws in an open position.

Referring to FIGS. 5-7, it is seen that each jaw 20 passes through a hole 51 in faceplate 21 and includes two pieces 48, 50 that are pivotally connected by pins 52 mounted on the back of faceplate 21 by a bracket 54. Compression springs 56 outwardly bias the rear extensions 57 of pieces 48, 50. Guidance surfaces 58 at the fronts of jaws 20 guide the corresponding circular extension 23 of cassette 12 into the tightly fitting circular cavity provided by curved surfaces 60. Rear extensions 57 of pieces 48, 50 have cam surfaces 62 leading to region 64 (FIG. 6) between extensions 57 when they are separated by pins 68 on supports 66 of movable support plate 26.

OPERATION

Before cassette 12 can be mounted on apparatus 10, jaws 20 must be opened by separating support plate 26 from faceplate 21 so that pins 68 are moved out of regions 64, permitting jaws 20 to be opened. This is done by increasing the air pressure in bladder 40, causing support plate 26 to be moved backward from faceplate 21. Cassette 12 is mounted on apparatus 10 by aligning the cassette's three circular extensions 23 with respective jaws 20. Circular extensions 23 are guided by guidance surfaces 58 into the regions between curved surfaces 60. The air pressure is bladder 40 is lowered, and springs 44 push plate 26 and sensors 14 toward faceplate 21. Referring to FIG. 7, as pins 68 approach cam surfaces 62, they push the rear extensions 57 of jaws 20 open, causing jaws 20 to tightly engage circular extensions 23, thereby locking cassette 12 into an insertion position in which openings 15 are accurately aligned with sensors 14 along insertion axes 70. This occurs before the tips of sensors 14 reach the rear portions of the cylindrical projections defining openings 15. As support plate 26 moves closer to faceplate 21, sensors 14 move into openings 15, and O-rings 22 sealably engage cylindrical surfaces 24.

With this mechanism, the operator thus brings cassette 12 into rough alignment with jaws 20, and pressure sensors 14 cannot contact cassette 12 until after the cassette has been locked into the insertion position with openings 15 accurately aligned with sensors 14 along insertion axes 70. Cassette 12 is then brought into position by springs 44 with a controlled force. This prevents damage to either sensor 14 or to cassette 12 around the opening 15 that might occur from possible jamming if the operator were to attempt to directly align sensors 14 with openings 15 when mounting cassette 12 on the machine.

OTHER EMBODIMENTS

Other embodiments of the invention are within the scope of the following claims.

What is claimed is:

1. The combination comprising

A fluid flow cassette having a circular opening having an associated cylindrical surface mating with and sealably engaging a pressure sensor, and apparatus for supporting said cassette, said apparatus comprising a support carrying said sensor mounted thereon, locking means operably connected to said support to lock said cassette into an insertion position with its opening aligned with but spaced from said sensor, the axis of said cylindrical surface being aligned with an insertion axis passing through said sensor, moving means operably connected between said locking means and said support to move said sensor relative to said opening along said insertion axis to cause said sensor and opening to be brought together and said cylindrical surface to sealably engage and mate with said sensor, preventing means operably connected to said locking means to prevent said sensor and cassette from being brought close enough for said sensor to contact said cassette until after said cassette as been locked into said insertion position, and release means to separate said support from said cassette.

2. The apparatus of claim 1 wherein said support is slidably mounted relative to said locking means.

3. The apparatus of claim 2 wherein said locking means includes a faceplate and jaws that extend from said faceplate and are adapted to engage said cassette.

4. The apparatus of claim 3 wherein said locking means includes means to permit said jaws to be opened only if said sensor is spaced from said faceplate and to close said jaws around said cassette before said sensor reaches said opening during travel of said support toward said faceplate.

5. The apparatus of claim 4 wherein said faceplate has a rear side, and said jaws are pivotally mounted about a pivot secured to said faceplate and have extensions on the rear side of said faceplate that separate when said jaws are closed and come together when said jaws are open, and wherein said means to prevent comprises pins that are mounted on said support and are aligned with said extensions in position to prevent said support from moving close enough to said faceplate for said sensors to contact said cassette unless said extensions are separated and said jaws are closed.

6. The apparatus of claim 5 wherein there are camming surfaces on said extensions to cause said extensions to be separated by said pins as said support moves toward said faceplate.

7. The apparatus of claim 3 wherein the jaws have guidance surfaces on the front portions to guide circular extensions of said cassette into similarly shaped cavities that are between the opposing jaws and tightly fit around the extensions when the jaws are closed.

8. The apparatus of claim 3 wherein said faceplate has a rear and said support is mounted on rods extending from the rear of said faceplate, and there are springs biasing said movable support toward said faceplate.

9. The apparatus of claim 8 wherein said support is a support plate and said release means comprises pneumatic means for separating said faceplate and said support plate.

10. The apparatus of claim 9 wherein said pneumatic means includes an inflatable bladder positioned between said support plate and said faceplate.

11. The apparatus of claim 2 wherein said sensor has an O-ring adapted to sealably engage said cylindrical surface.

12. The apparatus of claim 11 wherein said sensor is mounted for slight lateral shifting in a direction transverse to said insertion axis to permit centering of it within said circular opening.

13. The apparatus of claim 9 wherein said support plate has a rear and there are strengthening ribs on the rear of said plate.

14. The apparatus of claim 3 wherein said faceplate has a front and there are guidance ribs on the front of said faceplate adapted to engage sides of said cassette.

* * * * *